(12) United States Patent
Kugelmann et al.

(10) Patent No.: US 8,557,571 B2
(45) Date of Patent: Oct. 15, 2013

(54) REACTOR AND REACTOR UNIT WITH HOLLOW FIBERS

(75) Inventors: Franz Kugelmann, St. Wendel-Bliesen (DE); Paul Hengster, Innsbruck (AT); Raimund Margreiter, Reith (AT); Bernd Nederlof, St. Wendel (DE); Massimo Fini, Mirandola (IT); Ciro Tetta, Mirandola (IT); Thomas Wild, St. Wendel (DE); Micaela Yakubovich, Bad Homburg (DE); Michael Paul, Eppelborn (DE); Marco Caronna, Modena (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1053 days.

(21) Appl. No.: 11/794,234

(22) PCT Filed: Dec. 22, 2005

(86) PCT No.: PCT/EP2005/013906
§ 371 (c)(1),
(2), (4) Date: Feb. 8, 2008

(87) PCT Pub. No.: WO2006/069737
PCT Pub. Date: Jul. 6, 2006

(65) Prior Publication Data
US 2008/0145926 A1    Jun. 19, 2008

(30) Foreign Application Priority Data

Dec. 27, 2004 (DE) .......................... 10 2004 062 828
May 9, 2005 (DE) .......................... 10 2005 021 305

(51) Int. Cl.
*C12M 1/12* (2006.01)

(52) U.S. Cl.
USPC .................. 435/297.4; 210/321.8; 435/289.1

(58) Field of Classification Search
USPC .............. 435/289.1, 297.4, 298.2; 210/321.8, 210/321.81, 321.89, 321.9
See application file for complete search history.

(56) References Cited

U.S. PATENT DOCUMENTS

| 4,440,853 A | 4/1984 | Michaels et al. |
| 4,647,539 A | 3/1987 | Bach |
| 4,806,246 A | 2/1989 | Nomura |
| 5,057,428 A * | 10/1991 | Mizutani et al. ........... 435/293.2 |

(Continued)

FOREIGN PATENT DOCUMENTS

| DE | 198 03 534 A1 | 8/1999 |
| EP | 1 078 982 A2 | 2/2001 |

(Continued)

*Primary Examiner* — Michael Marcheschi
*Assistant Examiner* — Shanta G Doe
(74) *Attorney, Agent, or Firm* — Jacobson Holman PLLC

(57) ABSTRACT

A reactor has a reactor unit with a first chamber and a second chamber, with the first chamber being formed by the interior of a housing and the second chamber being formed by the interior of a plurality of hollow fibers arranged in the housing. The hollow fibers are arranged in the housing such that their density in at least one region of the first chamber does not exceed 10 fibers/mm$^2$, based on the cross-sectional area of the first chamber. The reactor unit can include two casting compounds, in which a portion of the hollow fibers are embedded and between which another portion of the hollow fibers extends. The length of at least some or all of the hollow fibers is at least 0.5% greater than the distance of the casting compounds.

43 Claims, 12 Drawing Sheets

(56) References Cited

U.S. PATENT DOCUMENTS

| | | |
|---|---|---|
| 5,437,998 A | 8/1995 | Schwarz et al. |
| 5,622,857 A * | 4/1997 | Goffe .................. 435/378 |
| 5,882,918 A * | 3/1999 | Goffe .................. 435/286.6 |
| 5,955,353 A | 9/1999 | Amiot |
| 6,001,585 A | 12/1999 | Gramer |
| 6,273,849 B1 | 8/2001 | Scherer |
| 6,832,981 B2 | 12/2004 | Witthaus et al. |
| 2002/0168758 A1 | 11/2002 | Martinez et al. |
| 2003/0038074 A1* | 2/2003 | Patil .................. 210/321.74 |
| 2003/0129736 A1* | 7/2003 | Mitrani .................. 435/284.1 |
| 2003/0203478 A1 | 10/2003 | Cadwell |
| 2004/0048366 A1 | 3/2004 | Stroh et al. |

FOREIGN PATENT DOCUMENTS

| | | |
|---|---|---|
| EP | 1 270 079 A2 | 1/2003 |
| EP | 1 333 086 A1 | 8/2003 |
| JP | 1 222768 A | 9/1989 |
| JP | H03-103170 | 4/1991 |
| JP | 2000-515391 | 11/2000 |
| JP | 2002-112763 | 4/2002 |
| JP | 2004-166717 | 6/2004 |
| WO | WO 98/53046 | 11/1998 |
| WO | WO 03/105663 A2 | 12/2003 |
| WO | WO 2004/050864 A1 | 6/2004 |

* cited by examiner

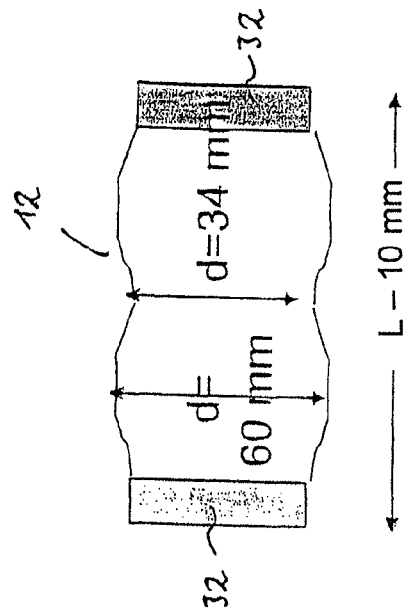
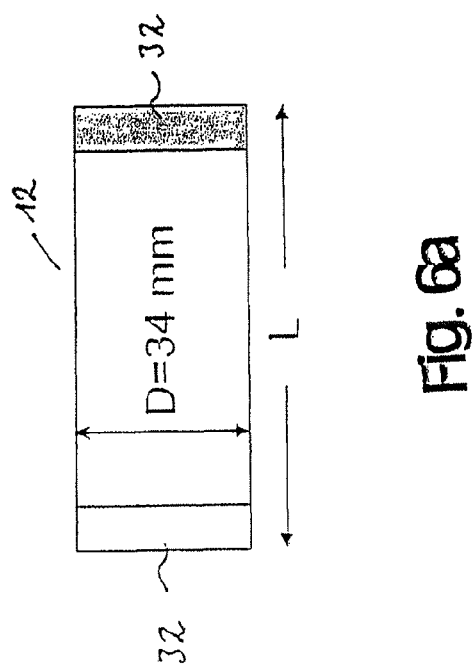
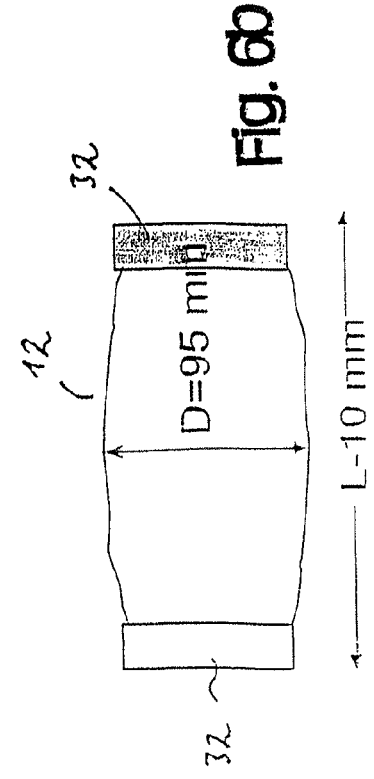

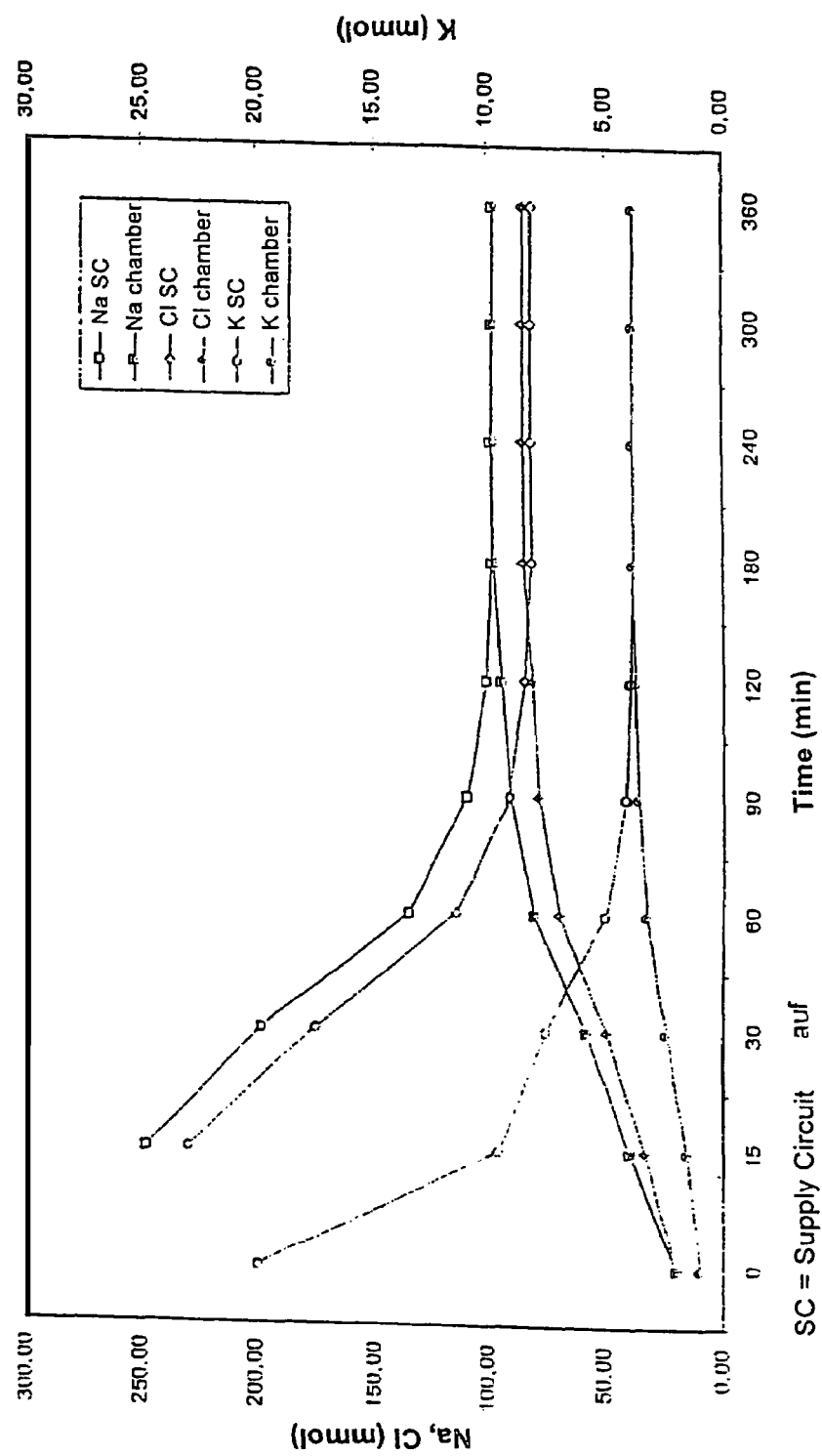

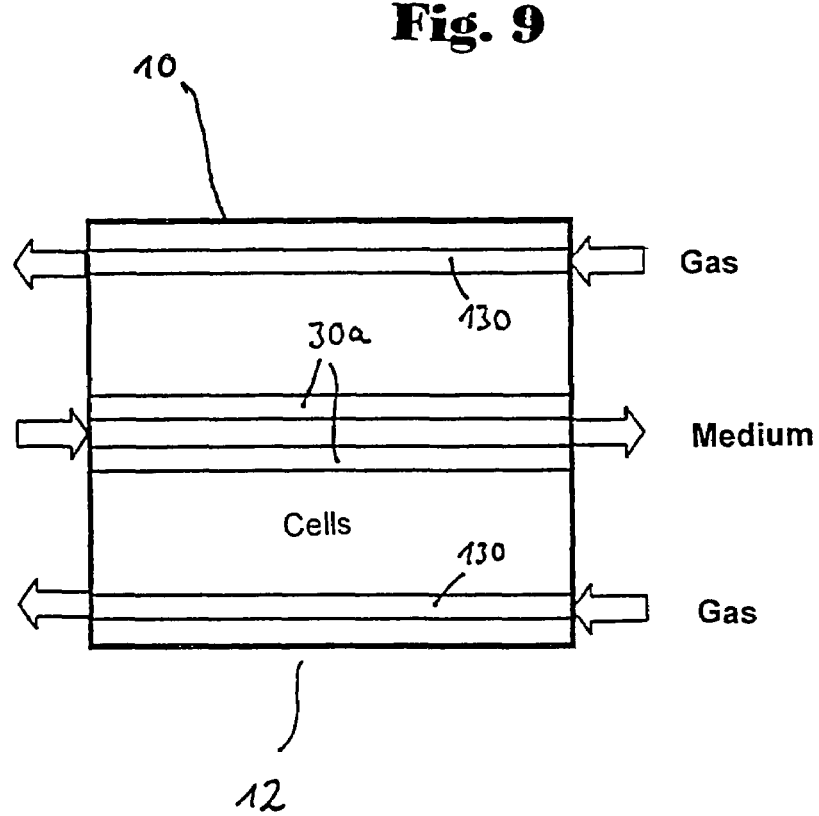

REACTOR AND REACTOR UNIT WITH HOLLOW FIBERS

CROSS-REFERENCE TO RELATED APPLICATION

This is a national stage of PCT/EP05/013906 filed Dec. 22, 2005 and published in German.

BACKGROUND OF THE INVENTION

1. Field of Invention

This invention relates to a reactor unit with a first chamber and a second chamber, wherein the first chamber is formed by the interior of a housing, and wherein the second chamber is formed by the interior of a plurality of hollow fibers disposed in the housing.

2. Description of Prior Art

Different types of such reactor units are known and are used, for instance, to grow human or animal cells of different origin or are employed, for instance, in the artificial liver or pancreas replacement therapy.

From U.S. Pat. No. 5,437,998 a reactor is known, which includes a rotatably mounted reactor unit which contains a medium with cells to be grown. Supplying the cell medium with oxygen and discharging the $CO_2$ formed is achieved by means of a permeable wall of the reactor unit.

From WO 03/105663 A2, a liver support system is known, which includes a reactor unit with a first chamber and a second chamber, wherein the first chamber is formed by the interior of a housing and the second chamber is formed by the interior of hollow fibers of a bundle of hollow fibers accommodated in the housing. The hepatocytes are contained in the first chamber. In one embodiment of the reactor described, the blood plasma is passed through the interior of the hollow fibers, i.e. through the second chamber. The mass transfer is effected via the hollow fiber membranes. The hollow fibers are designed straight and extend in longitudinal direction of the housing. From WO 04/050864 A1 a bioreactor is known, in which there is provided a chamber containing the cells to be grown, which by means of a membrane is separated from a supply and discharge conduit carrying a nutrient medium.

As explained above, the above-mentioned reactor units can for instance be used to grow cells. Another field of use is therapy, for instance the liver and pancreas replacement therapy. Prior art reactor units thus for instance have a first chamber for cultivating cells, through which extends a supply circuit formed by the second chamber, through which flows a nutrient medium or blood or blood components. The second chamber generally is formed by a bundle of hollow fiber membranes, wherein substances are exchanged with the medium in the first chamber via the membranes of the hollow fibers. It is usually provided that larger units, such as e.g. cells, cannot pass the membrane of the hollow fibers. By means of such a reactor unit, the cells in the first chamber can be supplied with nutrient, and metabolic products can be discharged. In the case of the above-mentioned use of the reactor unit as artifical liver, substances from the blood are exchanged with the chamber, which substances then are metabolized by liver cells.

The above-mentioned processes require a good mass transfer between the first chamber and the second chamber of the reactor unit. It is the object of the present invention to develop a reactor unit as mentioned above such that the reactor unit has improved mass transfer properties as compared to known reactor units.

SUMMARY OF THE INVENTION

This object is solved by a reactor unit with the features described herein. Accordingly, it is provided that the hollow fibers are arranged in the housing such that their density in at least one region of the first chamber does not exceed 10 fibers/mm$^2$, based on the cross-sectional area of the first chamber. It was found that the mass transfer between the first and the second chamber can be effected optimally when the hollow fibers do not exceed a certain density based on the cross-section of the first chamber. It was noted that a good exchange is effected when the density of the fibers does not have the maximum possible value, but lies below such value. A most dense packing of the fibers as preferred in hemodialzers is not advantageous here. A minimum density is obtained when ensuring the supply capacity, which also depends on the total exchange surface.

In a hollow fiber with an outside diameter of about 250 μm, the maximum fiber density is 12 fibers/mm$^2$. It was found that a particularly favorable mass transfer is achieved when the density of the fibers based on the cross-sectional area of the first chamber does not exceed the value of 10 fibers/mm$^2$.

Particularly advantageously, the density of the hollow fibers per unit area in at least one region of the first chamber lies in the range from 0.2 to 10 fibers/mm$^2$, preferably in the range from 0.5 to 6 fibers/mm$^2$ and particularly preferably in the range from 1 to 4 fibers/mm$^2$. These densities can be realized at least at one point of the first chamber.

The fiber densities indicated here and in the following refer to a uniform fiber density based on 1 cm$^2$.

The inventive density of the hollow fibers of the reactor unit per unit area can be realized on the one hand in that the fibers are already potted in the corresponding density, i.e. are embedded in casting compounds in their terminal regions. Furthermore, it is possible to pot the fibers in the form of their densest possible packing and then reduce the distance between the two casting compounds in the chamber, so that the distance of the potting surfaces is less than the length of the portion of the fibers located between the casting compounds. In this case, the fibers do not extend straight between the potting surfaces, but curved, for instance spindle-shaped.

Thus, it is conceivable that the density of the fibers based on the cross-sectional area of the first chamber is changing in longitudinal direction of the fibers. This is the case, for instance, when the fibers are potted in their densest packing, but the distance between the surfaces of the casting compounds facing each other is smaller than the length of the fiber portions located between the casting compounds. Alternatively, it can also be provided that the density of the fibers based on the cross-sectional area of the first chamber is constant in longitudinal direction of the fibers. Such embodiment is conceivable when the fibers are potted in the desired density, which lies below the maximum possible density.

In principle, it is possible that one or also more than one casting compound is disposed in the reactor unit, in which a portion, usually the end portion of the hollow fibers is embedded. A casting compound can be provided when the fibers for instance have a U-shaped flow.

Of course, it is also possible that the reactor unit includes two casting compounds, which are facing each other and in which one portion, preferably the end portion of the hollow fibers is embedded and between which a further portion of the hollow fibers extends.

As explained above, it can be provided that the hollow fibers extend straight or also curved between the casting compounds, so that for instance a bulged or spindle-shaped bundle of hollow fibers is obtained. The fibers are filling the volume of the first chamber to a greater extent than in the case of an elongated, straight fiber flow.

As explained above, an advantageous aspect of the invention consists in that the length of the portion of at least some or all hollow fibers located between the casting compounds is at least 0.5% greater than the distance of the surfaces of the casting compounds facing each other. Particularly preferably, the length of said portions of at least some or all hollow fibers is at least 1% and preferably at least 3% greater than said distance of the potting surfaces.

It is possible to constrict the hollow fibers with suitable means such that the density of the fibers based on the cross-sectional area of the first chamber is increased. In principle, the hollow fibers or the spindles formed by the same can be constricted by O-rings, for instance, so that the density can again be regulated upwards.

In a further aspect of the invention it is provided that the reactor unit includes a third chamber, which is formed by hollow fibers which serve the transfer of at least one gaseous medium via the hollow fiber membrane. There can be realized a circuit for the gas transfer. In addition to the hollow fibers forming the second chamber, which preferably are traversed by a liquid, it can thus be provided that further hollow fibers extend through the interior of the housing or of the first chamber. Preferably, a plurality of such hollow gas transfer fibers forming the third chamber are provided.

The arrangement of the hollow gas transfer fibers largely can be effected as desired. It is conceivable, for instance, that the hollow fibers forming the second chamber, which in operation preferably are traversed by a liquid medium, are disposed in a central portion of the reactor unit, and the hollow gas transfer fibers, which in operation preferably are traversed by a gaseous medium, are disposed in peripheral regions of the reactor unit.

In a further aspect of the invention it is provided that the hollow gas transfer fibers have a larger inside and/or outside diameter than the hollow fibers forming the second chamber.

In a preferred aspect of the invention it is provided that the hollow gas transfer fibers forming the third chamber are designed such that a transfer of oxygen via the membrane is possible. In this case, the hollow gas transfer fibers forming the third chamber can be used for oxygenating the medium contained in the first chamber or the cells contained therein.

The hollow gas transfer fibers forming the third chamber can for instance be made of PTFE. It is conceivable, for instance, to use a hydrophobic gas transfer membrane for the hollow gas transfer fibers.

The invention furthermore relates to a reactor unit with a first chamber and a second chamber, wherein the first chamber is formed by the interior of a housing and wherein the second chamber is formed by the interior of a plurality of hollow fibers disposed in the housing. It is provided that at least two casting compounds are disposed in the reactor unit, in which one portion, preferably the end portion of the hollow fibers is embedded and between which a further portion of the hollow fibers extends, wherein the length of the hollow fiber portion of at least some or all hollow fibers located between the casting compounds is at least 0.5% greater than the distance of the potting surfaces facing each other. In this way, a smaller fiber density per unit area is obtained than for the case that the distance of the potting surfaces facing each other corresponds to the length of that portion of the hollow fibers which extends between the same. Particularly advantageously, such reactor unit is designed as described herein.

The flow of the hollow fibers in the housing largely can be as desired. It is conceivable that the hollow fibers are arranged such that the medium flowing through the same is guided in one direction or in at least two different directions. In the latter case, the medium flowing through the hollow fibers thus undergoes at least one change in direction. It is conceivable, for instance, that the flow path of the medium flowing through the hollow fibers is substantially U-shaped or that U-shaped hollow fibers are being used.

If there is at least one change in direction, an advantageous aspect of the invention is obtained in particular when the mass transfer between the two chambers should at least also be effected by convection. The convective mass transport is directly proportional to the pressure difference across the hollow fiber membranes. The pressure drop in the hollow fibers is directly proportional to the length of the fiber and inversely proportional to the diameter of the fiber in the fourth power. Thus, if the flow path of the medium flowing through the hollow fibers undergoes a change in direction at least once, for instance a reversal of direction, in which it is guided forth and back e.g. at least once, the total path through the housing is increased correspondingly. This results in a correspondingly higher pressure in the hollow fiber membranes and leads to an increase of the pressure difference across the hollow fiber membranes and thus to an increase of the convective exchange.

Particularly advantageously, the inlet and outlet of the hollow fibers are disposed on the same side of the housing. It is possible that the flow path of the medium guided through the hollow fibers is U-shaped or also has several changes in direction. It is possible to adjust the pressure difference between the first chamber and the second chamber or between the media contained in the same such that said pressure difference is zero at the point of reversal of the hollow fibers. Before this point of reversal, the pressure difference leads to a convection from the hollow fibers into the first chamber and in the flow path adjoining the point of reversal to a convection from the first chamber into the second chamber, i.e. from the medium contained in the housing into the hollow fibers.

As explained above, the hollow fibers can be arranged in the housing such that a medium flowing through the hollow fibers follows a substantially U-shaped flow path.

The hollow fibers can be substantially U-shaped. It is likewise conceivable that the hollow fibers are designed straight and at their two terminal regions are embedded in casting compounds, the flow path being designed such that the medium first of all traverses one or more hollow fibers, in whose terminal region a change in direction is effected, and then flows back through other hollow fibers.

The housing can have a rotationally symmetric, preferably cylindrical design.

In a further aspect of the invention it is provided that proceeding from the inlet up to a region in which the direction of the flow of the hollow fibers is changed the hollow fibers extend in a first direction, and from the region of the change in direction extend in a second direction different from the first direction, wherein the hollow fiber portions extending in the first direction radially extend on the inside, and the hollow fiber portions extending in the second direction radially extend on the outside relative thereto. Such embodiment is considered, for instance, when the hollow fibers already are embedded in the casting compounds with a relatively small density. It is conceivable, for instance, that the pressure difference between the first and the second chamber is chosen such that there is a spatial separation between supplying and withdrawing hollow fibers. This can provide for a thorough mixing. It is conceivable, for instance, to arrange the supplying fibers radially on the inside and the withdrawing fibers radially on the outside parallel thereto. In principle, different aspects are conceivable, such as the reverse arrangement with supplying fibers located on the outside and withdrawing fibers located on the inside.

As explained above, the pressure drop in the hollow fiber is inversely proportional to the diameter of the fiber in the fourth power. In view of this it is favorable to chose a rather small fiber diameter. Preferably, it is provided that the inside diameter of the hollow fibers is not more than 300 µm, preferably not more than 200 µm and particularly preferably about 100 µm.

A high porosity of the hollow fiber membranes likewise provides for a good mass transfer. The hydraulic permeability of the membrane should be at least 200 ml/mmHg×h×m$^2$, preferably at least 500 ml/mmHg×h×m$^2$.

In a further aspect of the invention it is provided that the cut-off of the membrane forming the hollow fibers lies in the range between $10^4$ Da and $10^7$ Da, preferably in the range between $10^5$ Da and $10^6$ Da. A particularly preferred cut-off lies in the range from 700,000 to 900,000 Da. Different porosities or cut-offs are of course possible. In dependence on the intended use, the use of hollow fiber membranes with little porosity is also conceivable.

Particularly advantageously, the reactor unit is designed as a disposable unit.

Furthermore, the reactor unit advantageously is constructed of materials which can be sterilized with steam. The used materials preferably correspond to those materials which are also used in dialysis filters. Thus, it is conceivable to make the housing of PP and/or the casting compound of polyurethane and/or the hollow fibers of polyaryl ether sulfones, preferably of polysulfones, and particularly preferably of polysulfones hydrophilized with PVP. In a further aspect of the invention, all materials are dimensionally stable when sterilized with steam at 121° C.

The invention furthermore relates to a reactor with at least one inventive reactor unit, wherein the reactor unit is rotatably mounted. A particularly good mass transfer between the first and the second chamber is obtained when the reactor unit is not standing still, but is rotating. Correspondingly, an advantageous aspect of the invention relates to a reactor with a rotatably mounted reactor unit. There can be provided corresponding drive means by which the reactor unit is put into a rotary movement.

In a further aspect of the invention it is provided that the reactor not only includes one, but a plurality of reactor units. This plurality of reactor units can be interconnected as desired. It is conceivable, for instance, to arrange the reactor units in series, so that the outlet of one reactor unit forms the inlet of another reactor unit. It is likewise conceivable to arrange the reactor units in parallel and supply the same for instance with an identical charge, such as exactly the same nutrient solution.

Said series connection can be designed such that a flow path between the reactor units extends in one direction, i.e. the outlet of a first reactor unit forms the inlet of a second, succeeding reactor unit. It is also conceivable that the outlet of said second reactor unit in turn forms the inlet for the first reactor unit, so that a mass transfer takes place in two directions.

By combining the reactor units in a serial and parallel arrangement, highly innovative applications can be realized. Particularly advantageously, a reactor with a plurality of reactor units can be employed for simulating "metabolic processes in vivo".

In a further aspect of the invention it is provided that the reactor is constructed without floating ring seal. When the flow direction through the hollow fibers is reversed at least once, the inlet and the outlet of the hollow fibers can be located on the same side of the housing. In particular in this case, it is possible to design the reactor unit without floating ring seal, as described for instance in EP 1 270 079 A2 and DE 198 03 534 C2 for the example of a cell separator. In so far, reference is made to these documents. Essential advantages are obtained for sterilizability and also for contamination safety, when a floating ring seal is omitted. In addition, the production costs for the reactor unit are decreased.

The invention furthermore relates to a method for effecting a mass transfer by means of one or more hollow fibers by using a reactor unit or a reactor as described herein, wherein the pressure in the second chamber formed by the interior of the hollow fibers and in the first chamber formed by the housing is adjusted such that the mass transfer through the hollow fibers is at least partly effected by convection. On this convective mass transfer a mass transfer by diffusion can be superimposed. The mass transfer by convection preferably is bidirectional and is considered in particular for medium-molecular and higher-molecular synthesis products or nutrients with a low diffusion rate.

In a further aspect it is provided that the pressure ratios between the first and the second chamber are chosen such that the convective mass transport in one portion of the hollow fibers is effected from the medium contained in the hollow fibers into the medium received in the housing and in another portion of the hollow fibers is effected in the opposite direction. In such aspect of the invention, there is a division into supplying and withdrawing hollow fibers or hollow fiber portions.

When employing the method for growing cells, it is conceivable for instance that hollow fibers or hollow fiber portions are provided, by means of which nutrients are supplied to the medium contained in the first chamber. Furthermore, hollow fibers or hollow fiber portions are provided, by means of which metabolic products from the medium contained in the first chamber are transferred into the hollow fibers and then are discharged.

The invention furthermore relates to a system with a reactor unit or a reactor as described herein, comprising a reservoir which is connected with the reactor unit such that from the reservoir medium can be introduced into the second chamber of the reactor unit formed by the hollow fibers or can be discharged from the same, comprising a delivery pump preferably designed as a peristaltic pump for delivering the medium, and comprising an oxygenator, by means of which the medium delivered can be enriched with oxygen. Oxygenation for instance is effected externally and is variably adjustable to the oxygen consumption. In this case, the supply of oxygen is effected via the blood plasma or the nutrient medium supplied. The oxygenator preferably is provided upstream of the reactor in flow direction of the medium. Furthermore, a heating means can be provided for heating the medium delivered. In principle, oxygenation can also be effected by means of gas-transfer hollow fiber membranes disposed in the reactor unit.

BRIEF DESCRCIPTION OF THE DRAWINGS

Further details and advantages of the invention can be taken from an embodiment illustrated in the drawing, in which:

FIG. 1: shows a perspective view of the reactor unit of the invention,

FIG. 2: shows a perspective view of the inventive reactor with housing,

FIG. 3: shows a schematic representation of the reactor unit of the invention,

FIG. 4: shows a further schematic representation of the reactor unit of the invention in another embodiment, FIG. 5: shows a schematic representation of the inventive mass transfer system with reactor, FIG. 6: shows schematic representations of different geometries of a prior art reactor unit and of inventive reactor units, FIG. 7: shows time-based concentration curves for urea, protein and various ions, when using a reactor unit of the invention, FIG. 8: shows time-based concentration curves for urea, protein and various ions, when using a reactor unit according to the prior art, FIG. 9: shows a schematic representation of an inventive reactor unit with hollow fibers forming the second chamber, which are traversed by a liquid medium, and with hollow gas transfer fibers for oxygenation, which form the third chamber, and FIG. 10: shows schematic representations of different arrangements of several reactor units connected in series or in parallel.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled'in the art from this detailed description.

Figure 1:
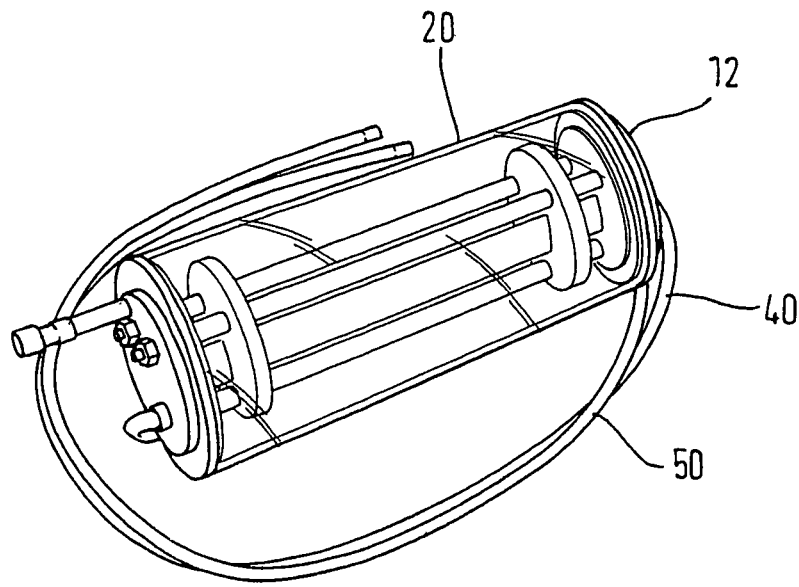

FIG. 1 shows a perspective view of the inventive reactor unit 12 designed as a disposable unit. The same consists of a housing 20, in which hollow fibers are arranged in the form of a hollow fiber bundle. Furthermore, an inlet 40 and an outlet 50 are provided, through which the medium traversing the hollow fibers is supplied or withdrawn.

Figure 2:
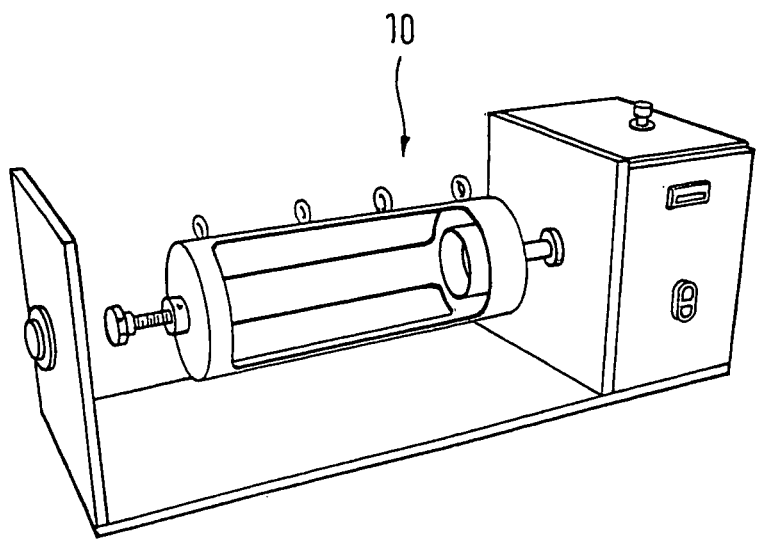

FIG. 2 shows the reactor 10 without reactor unit. There is illustrated the rotatable seat for fixing the reactor unit as shown in FIG. 1, which is put into a rotary movement by an electric motor. The seat or the reactor with reactor unit are accommodated in a heated housing.

Figure 3:
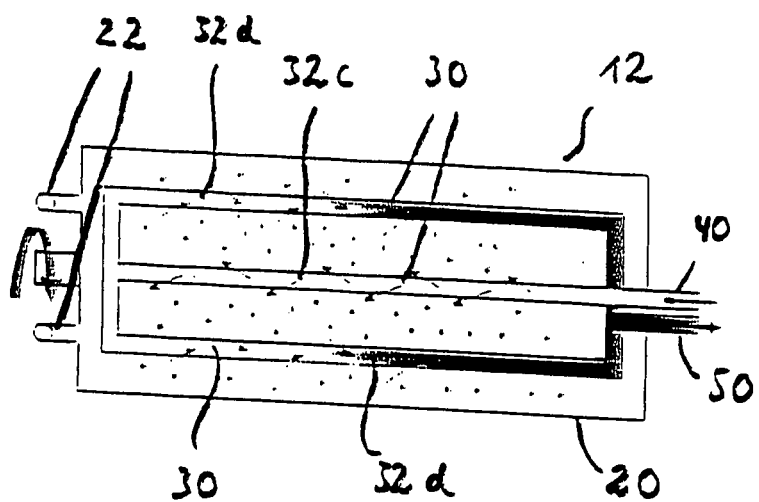

FIG. 3 shows a schematic representation of a rotatably mounted reactor unit 12. Conceivable fields of use are:
hepatocyte culture for different applications
artifical liver and pancrease replacement therapies
growing human and animal cells of different origin
production of antibodies
recovering substances from transfected yeasts and bacteria.

The dots shown in FIG. 3 represent cells contained in the first chamber of the reactor unit 12, which is defined by the housing 20. In the first chamber, hollow fibers 30 are arranged, which have an inlet 40 and an outlet 50. If it is a cell culture, nutrient medium is supplied via the inlet 40. For the case of a liver or pancreas replacement therapy, blood plasma is supplied via the inlet 40. The nutrient medium consumed or the blood plasma treated is withdrawn via the outlet 50.

As is furthermore shown in FIG. 3, the housing 20 includes two ports 22, which are used for filling, evacuating or sampling from the first chamber. It is conceivable to close the ports 22 upon filling or sampling. In principle, it is likewise conceivable to allow a continuous operation to the effect that medium is continuously introduced in or discharged from the first chamber via the ports 22. As can furthermore be taken from FIG. 3, hollow fibers 30 are provided centrally in the vicinity of the axis of rotation of the reactor unit 12, which form a hollow fiber portion 32c in which a comparatively high pressure exists, so that a convective mass transport from the portion 32c of the hollow fibers 30 into the first chamber of the reactor unit 12 defined by the housing 20 is effected, as indicated by arrows. In the terminal region of the portion 32c, a change in direction is effected first of all in a direction parallel to the end face of the housing 20 and then against the flow direction in the portion 32c. Due to the lower pressure in the hollow fibers 30 as a result of the pressure loss, a convective mass transport from the first chamber containing the cells into the hollow fibers 30 now is effected in the hollow fiber portions 32d, as is indicated by arrows in the vicinity of the hollow fiber portions 32d. Thus, a division into supplying hollow fibers or hollow fiber portions 32c and withdrawing hollow fibers or hollow fiber portions 32d is effected.

Finally, as can furthermore be taken from FIG. 3, the inlet 40 and the outlet of the hollow fibers are disposed on the same side of the housing 20, in the embodiment as shown in FIG. 3 on the right-hand end face of the cylindrical housing 20. Such design allows to provide a reactor without floating ring seal. The relative movement between stationary and moving parts can be achieved by the system known from EP 1 270 079 A2 and DE 198 03 534 C2.

The reactor unit 12 preferably is designed as a disposable unit. It can be an injection-molded construction, which includes the fundamental method steps analogous to the manufacture of a conventionally fabricated hemodialyzer, such as potting with PUR, cutting and sterilization. In this way, the reactor unit can be manufactured economically.

Figure 4:
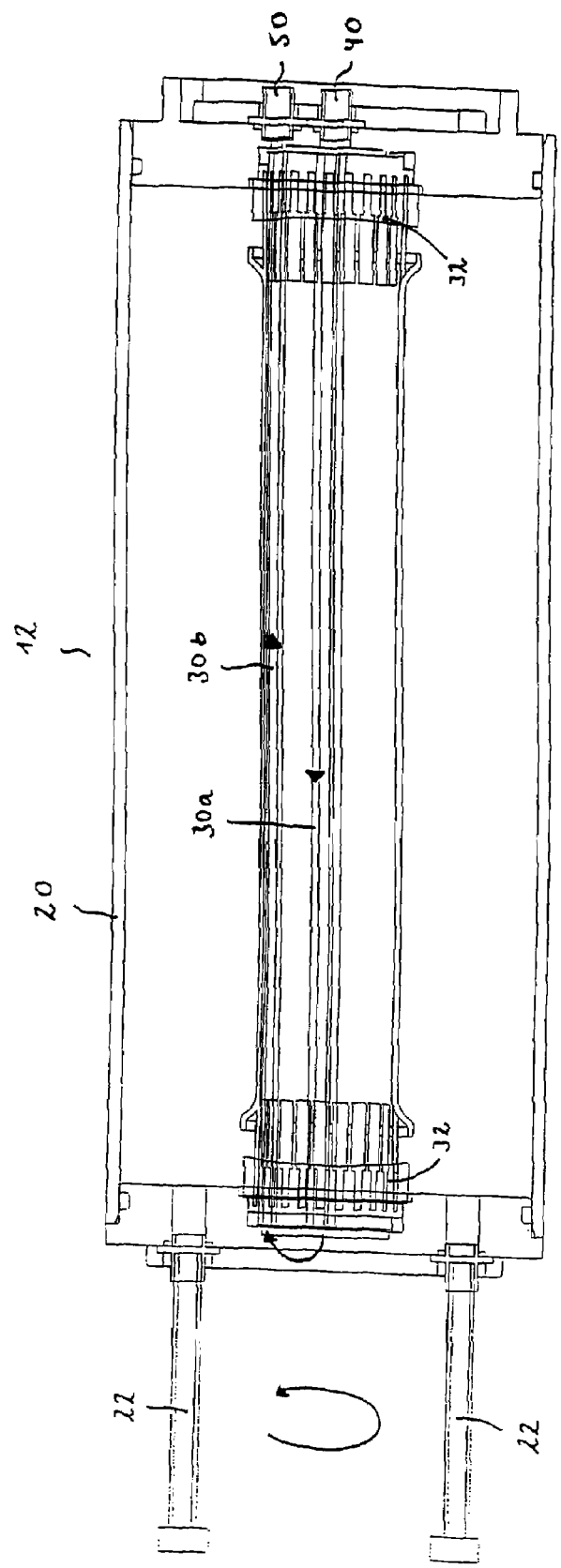

FIG. 4 shows another type of the reactor unit 12. In the first chamber defined by the cylindrical rotationally symmetric housing 20, human hepatocytes are contained in a suitable medium. In a radially central portion, the hollow fiber bundle is disposed, which consists of individual hollow fibers. The hollow fiber bundle includes a multitude of hollow fibers 30a disposed in the vicinity of the axis of rotation, of which only a few are shown by way of example. Furthermore, there is provided a plurality of hollow fibers 30b radially offset to the outside, which are arranged in the outer circumferential region of the hollow fiber bundle and of which there is likewise shown only one. Such embodiment is considered, for instance, when the hollow fibers already are embedded in the casting compounds with a relatively small density. The hollow fibers 30a, 30b are arranged in parallel and in their two terminal regions are fixed in casting compounds 32, which are fixed in the housing 20 in a suitable way. Via the inlet 40, medium flows into the hollow fibers 30a, traverses the same and exits the hollow fibers 30a at the terminal region thereof, which is illustrated on the left. Here, the medium gets into a flow space which connects the terminal regions of the hollow fibers 30a with the initial regions of the hollow fibers 30b. As is indicated by the arrow in the terminal region of the hollow fibers 30a, the flow direction of the medium is changed in the terminal region of the fibers 30a. Upon passing through the flow space, it flows into the hollow fibers 30b and through the same in the opposite direction than through the hollow fibers 30a. In their terminal region shown on the right, the hollow fibers 30b.are connected with the outlet 50, by means of which the correspondingly treated medium is withdrawn from the reactor unit 12. The medium can for instance be a nutrient medium or body fluids, such as blood or particularly preferably blood plasma.

The reactor unit shown in FIG. 4 can of course also be used for other purposes, such as for cell cultures.

The first chamber defined by the housing 20 includes two ports 22, which can serve to supply or withdraw of medium from the first chamber or to take samples.

As is furthermore shown in FIG. 4 and indicated by the arrow, the reactor unit 12 is rotated in operation, the axis of rotation extending parallel to the hollow fibers. Preferably, the hollow fibers 30a are arranged such that they are located in the vicinity of the axis of rotation, and the hollow fibers 30b are radially offset thereto to the outside. The pressure ratios can be chosen such that the pressure in the hollow fibers 30a lies above the pressure of the first chamber defined by the housing 20, and in the hollow fibers 30b below the pressure existing in the first chamber. At the point of reversal indicated by a curved arrow, it can be provided that there is no pressure difference between the first chamber and the second chamber. Different configurations of the pressure ratios are of course also conceivable.

The present invention differs from the embodiments in accordance with the prior art in that the reactor unit is designed such that the hollow fibers of the hollow fiber bundle disposed in the same are not arranged in a maximum possible density, but that the fiber density based on the cross-sectional area of the first chamber does not exceed 10 fibers/mm² or that the length of the hollow fiber portions accommodated between two casting compounds does not exceed the distance of the surfaces of the casting compounds facing each other by at least 0.5%.

FIG. 6a shows a reactor unit 12 designed according to the prior art in a schematic view. The hollow fiber membranes are enclosed in a plastics mesh and form a rigid cylindrical structure. The diameter of the hollow fiber bundle is D=34 mm. In the reactor unit as shown in FIG. 6a, the length between the two sectional areas of the casting compounds 32 is L=257 mm. With a number of 11,000 hollow fibers, the fiber density based on the cross-sectional area of the first chamber thus is about 12 fibers/mm².

FIG. 6b shows an embodiment of the schematically illustrated reactor unit 12 in accordance with the invention. As schematically indicated in FIG. 6b, the distance L of the sectional areas of the casting compounds 32 is reduced by 10 mm as compared to the embodiment in accordance with the prior art as shown in FIG. 6a. In this case, the hollow fibers are upset between the casting compounds 32 and form a spindle. In dependence on the distance of the potting surfaces, i.e. the surfaces of the casting compounds facing each other, smaller fiber densities are obtained than in the embodiment as shown in FIG. 6a. In the embodiment as shown in FIG. 6b, the largest diameter of the fiber bundle is 95 mm. Directly at the casting compounds 32, the fiber density corresponds to the one explained in conjunction with FIG. 6a. As a result of these dimensions, the fiber density in the inventive reactor unit 12 as shown in FIG. 6b lies in the range between 1.5 fibers/mm² and 12 fibers/mm².

FIG. 6c shows an embodiment in which the distance between the sectional areas of the casting compounds 32 corresponds to that distance shown in FIG. 6b, i.e., a distance of L - 10mm. However, the fiber bundle is constricted by an O-ring, so that the fiber density is again regulated upwards as compared to the embodiment as shown in FIG. 6b. In the vicinity of the constriction, the diameter of the fiber bundle is 34 mm. The maximum diameter of the fiber bundle is 60 mm, so that there is obtained a total density of the fibers per unit area in the range between 3.9 fibers/mm² and 12 fibers/mm².

Figure 11:
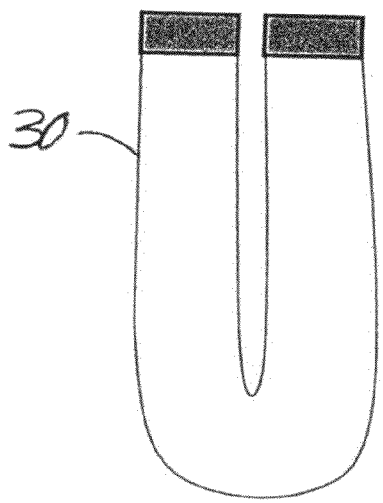
FIG. 11 is a schematic view of a U-shaped hollow fiber bundle according to an embodiment of the instant invention.
Figure 12:
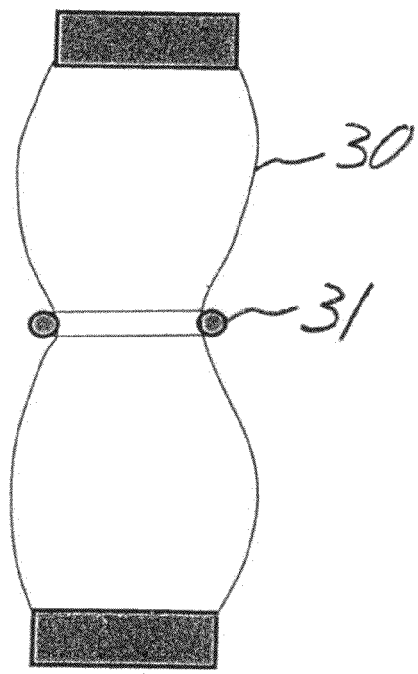
FIG. 12 is a schematic view of a hollow fiber bundle constricted by an O-ring according to an embodiment of the instant invention.

As indicated above, the flow of the hollow fibers in the housing largely can be as desired. It is conceivable that the hollow fibers are arranged such that the medium flowing through the same is guided in one direction or in at least two different directions. In the latter case, the medium flowing through the hollow fibers thus undergoes at least one change in direction. As depicted in FIG. 11, it is conceivable, for instance, that the flow path of the medium flowing through the hollow fibers is substantially U-shaped or that U-shaped hollow fibers are being used.

A comparison of FIGS. 7 and 8 illustrates the advantage involved in the inventive reactor unit as compared to a prior art reactor unit in terms of the mass transfer.

The concentration curves as shown in FIGS. 7 and 8 were obtained by means of the following test set-up or the following experimental procedure:

Upon assembly of the chambers, the same were checked for tightness and "bubble points" by applying pressure (compressed air).

For the experiments, 400 ml of exchange medium were prepared:

1 plasma bag+0.5 ml EDTA 100 mM (not with the experiments of FIG. 7)+50 ml of buffer B ad 400 ml with A.d. buffer B: urea 7.5 mg/ml, NaCl 22.5 mg/ml (385 mmol), KCl 1.25 mm/ml (16.7 mmol).

In all experiments, the hollow fibers were filled with exchange medium and upon decrease from the time "0" connected to the reactor unit or the first chamber thereof.

During the exchange experiments, the reactor unit was supplied with a flow rate of 200 ml/min at 25° C. and rotated with 15 rpm, in order to examine the exchange of samples by convection and diffusion.

Sampling was effected as follows:

For each determination, 2 ml of a sample were withdrawn by means of Monovette (Sarstedt 2 ml LH; CE 0197) at a point before entrance into the chamber and at the sample port 1 in the chamber. Before each sampling, about 2 to 3 ml of liquid were rinsed out of the collection ports, and only then the measurement sample was drawn. At the chamber, the sample withdrawn was replaced by water by means of the sample port 2. In the supply circuit formed by the hollow fibers, the sample withdrawn was replaced by the buffer reservoir.

In the test set-up for the experiments according to FIG. 7, the volume of the chambers was about 1.7 l. The hollow fiber membranes are stabilized by 2 plastic fibers. Due to the reduced distance of the casting compounds, the chambers are about 1 cm shorter than in the test set-up with which the test results of FIG. 8 were obtained. As a result, the membranes are upset and form a spindle-shaped structure filling the chamber volume.

In the test set-up leading to the test results as shown in FIG. 8, the chamber volume was about 1.8 l. The membranes are enclosed in a plastics mesh and form a rigid cylindrical structure.

As can be taken from a comparison of FIGS. 7 and 8, there is a distinct difference in the speed of the distribution of ions and organic molecules through the membranes with a pore size of 60 kd in dependence on the bundling of the membrane or the hollow fiber bundle.

Figure 7A:
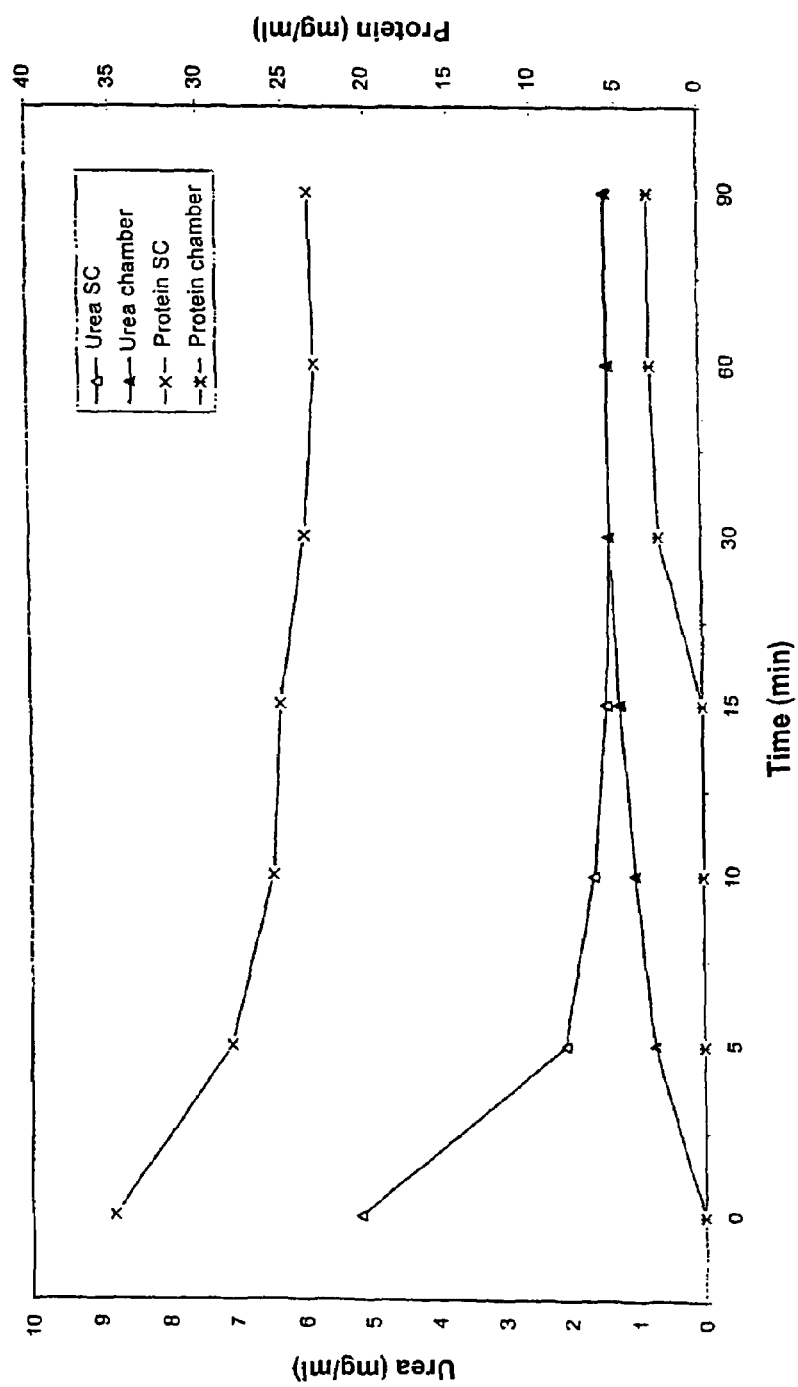
Figure 7B:
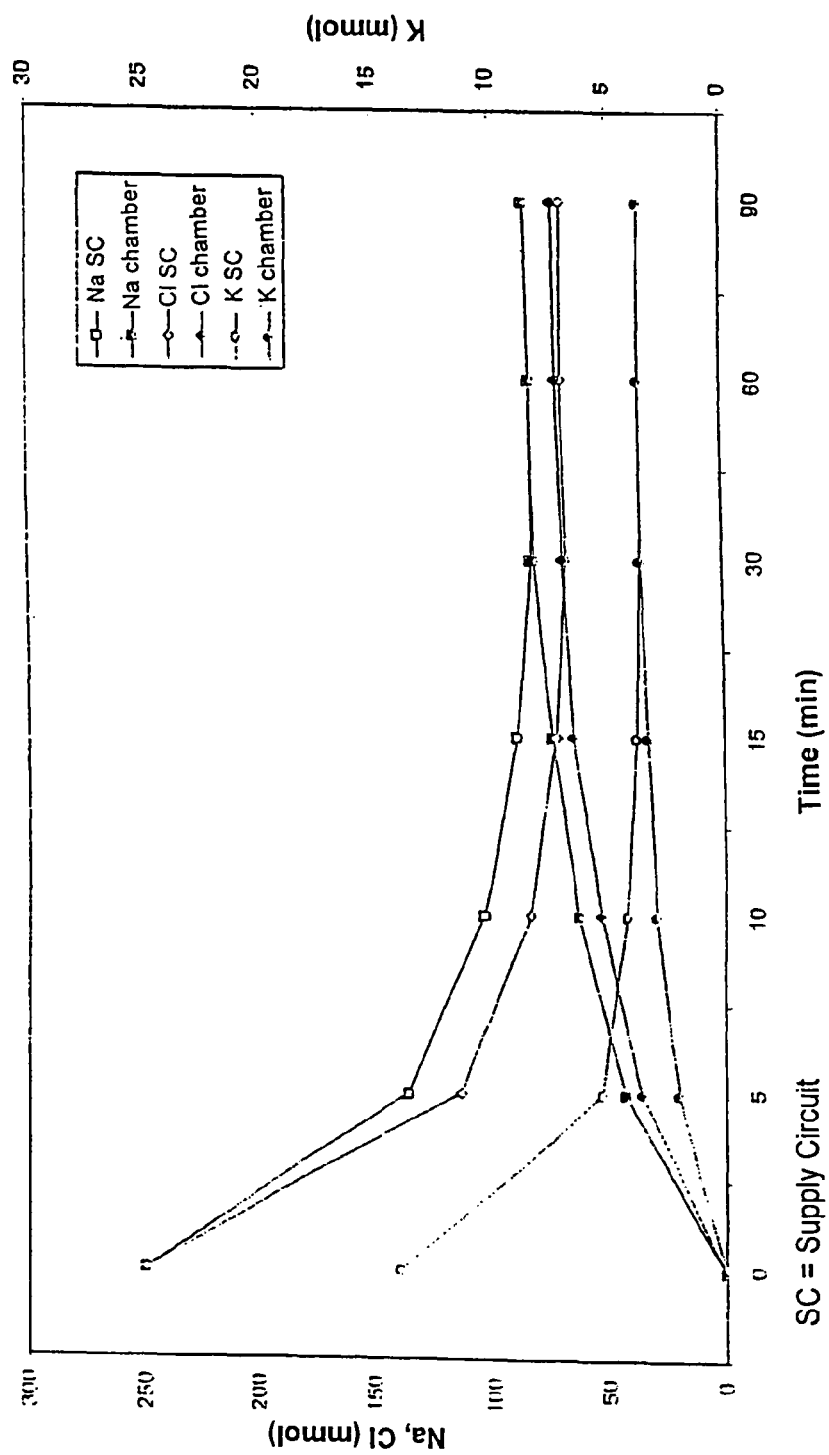

The upset open membrane (spindle shape) (fiber density: 1.5 fibers/mm²) largely fills the lumen of the first chamber and thereby effects a very good mass transfer. As can be taken from the illustrations of FIG. 7a, 7b, the material transfer between the hollow fibers and the first chamber is effected within the first few minutes upon starting the circuit. The complete transfer of concentrations in the case of ions and urea can be detected after about 30 to 60 minutes. Due to its high molecular weight, the protein exchanges more slowly and incompletely. In FIGS. 7 and 8, the abbreviations "SC" and "chamber" represent the concentrations in the supply circuit (SC), i.e. in the medium traversing the hollow fiber, and the concentrations in the first chamber of the reactor unit, respectively.

Figure 8A:
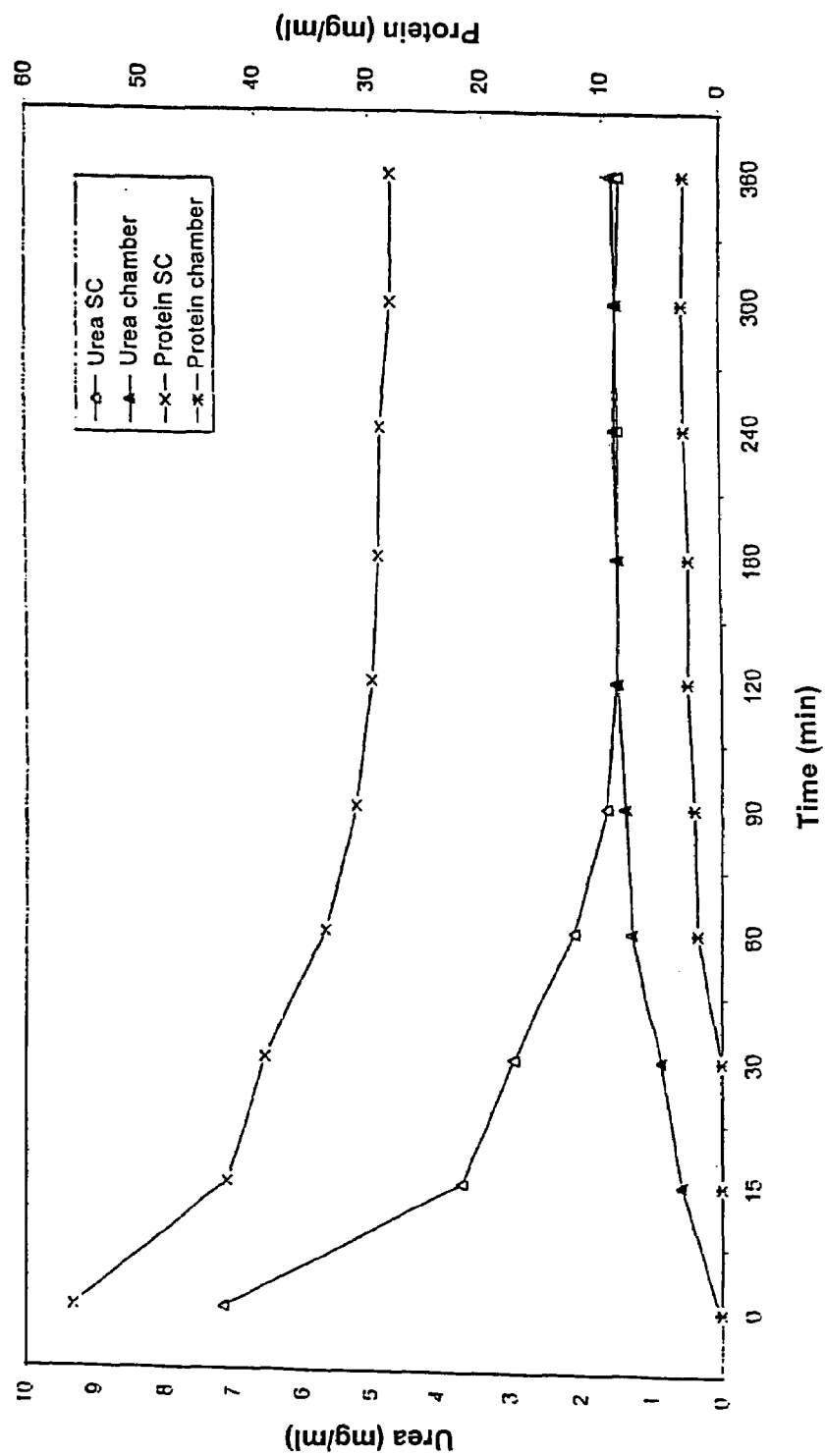

The ordinary, bundled membrane (cylindrical shape) (maximum fiber density), with which the test results as shown in FIG. 8 were obtained, forms a compact cylindrical strand of conduits with a relatively small transfer efficiency. As can be taken from the illustrations of FIG. 8a, 8b, the material transfer between the hollow fibers and the first chamber is effected at a distinctly slower rate than in FIG. 7. The complete smoothing-out of concentration in the case of ions and urea can be measured after 120 to 180 minutes and thus 3 to 4 times as slowly as in the spindle-shaped membranes in accordance with the invention. The protein likewise is exchanged slowly and incompletely.

As explained above, the reactor unit of the invention can be used for therapy, for instance for liver replacement or liver support therapy.

Figure 5:
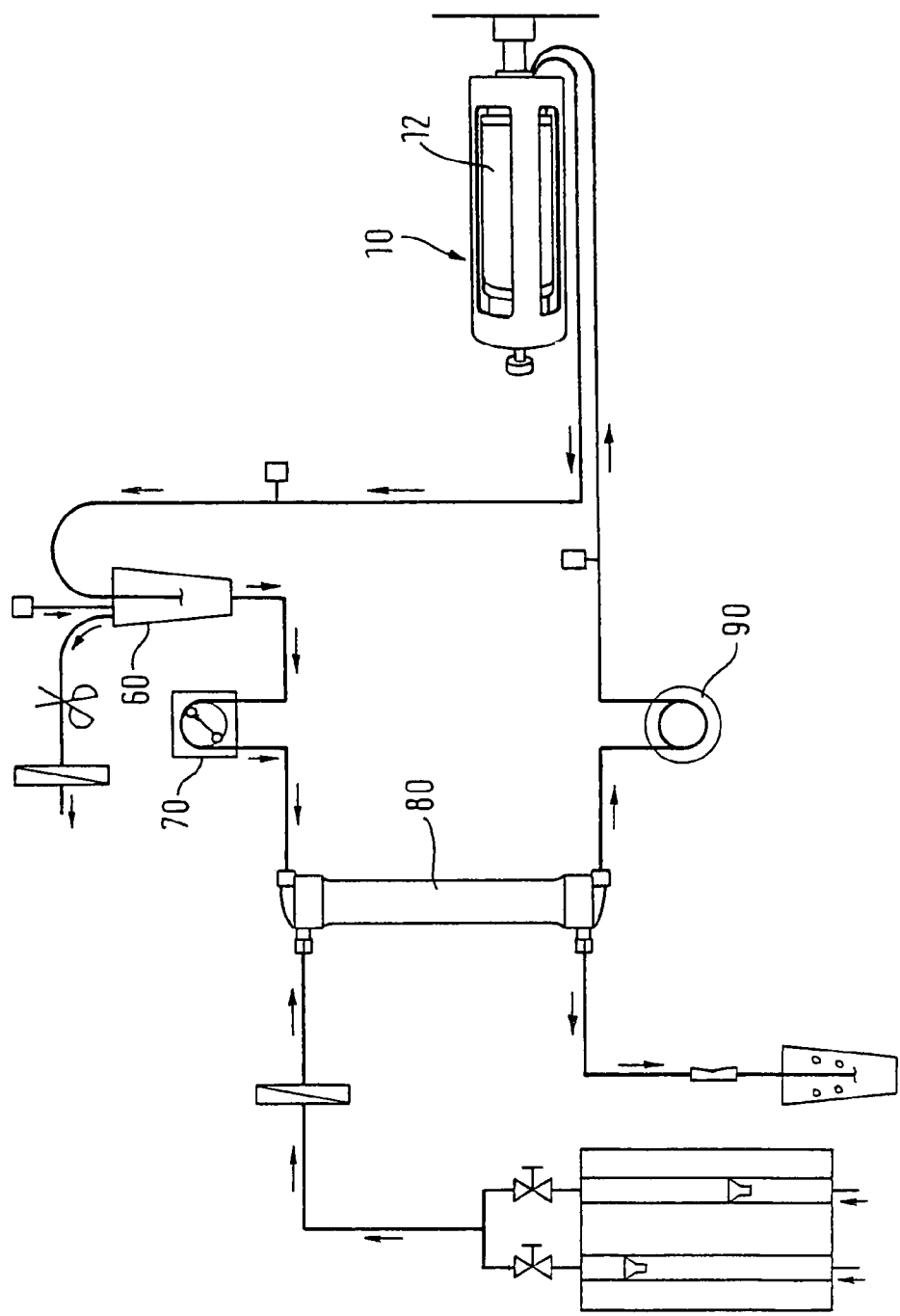

FIG. 5 shows a schematic representation of a total system for a liver support therapy. The same consists of a plasma reservoir 60 which contains blood plasma taken from the patient to be treated. By means of the peristaltic pump 70, plasma is withdrawn from the plasma reservoir 60 and supplied to the gas exchanger 80. In the gas exchanger 80, the supply of oxygen is effected via an oxygen source and a sterile filter, whereby the blood plasma is correspondingly enriched with oxygen. The gas exchanger likewise consists of two chambers, with oxygen flowing in one chamber and blood plasma flowing in the other chamber. The chambers are separated from each other by permeable membranes which permit the transfer of gases such as oxygen into the blood plasma. By means of the gas exchanger, not only oxygen can be supplied, but also other gases such as $CO_2$ or $N_2$ can be supplied or exchanged. In a particularly preferred aspect of the invention, the gas exchanger is designed as an oxygenator for exchanging oxygen.

Upon enriching the blood plasma with oxygen in the oxygenerator 80, the same passes through a heating device 90 and then flows into the reactor 10. The same includes the rotatably mounted reactor unit 12 of the invention, which is designed as a disposable unit. The reactor unit 12 is disposed in a rotatable seat of the reactor 10 and is put into a rotary movement during operation of the system. The axis of rotation coincides with the longitudinal axis of the reactor unit 12. The reactor is accommodated in a heated housing, as can be taken from FIG. 2 and FIG. 5. The system is designed without floating ring seal.

In contrast to the construction as shown in FIG. 5, the peristaltic pump 70 can also be disposed at another point of the circuit. An arrangement behind, i.e. downstream of the reactor 10 is also conceivable, for instance.

As a further component, the arrangement as shown in FIG. 5 can preferably optionally include a heating device in flow direction before the reactor 10, by means of which the medium supplied to the reactor 10 is heated.

A few advantageous aspects of the invention will be represented below:

As hollow fibers, there can preferably be used polysulfone plasma fibers with a large available exchange surface, preferably in the range from 0 to 2 $m^2$ with preferably variably adjustable porosity up to 900,000 MG. As stated above, the mass transport preferably chiefly is effected by means of convection to increase the bidirectional exchange through the hollow fiber membranes.

In dependence on the properties of the cells or substances to be exchanged, hydrophilic and/or hydrophobic membranes can be used for the hollow fibers.

As stated above, a separation of the supplying fibers from the withdrawing fibers can be effected. As a result, fiber bundles can variably be assigned inside the reactor. As an example, supplying and withdrawing fibers can be arranged centrally. It is also conceivable that supplying fibers are arranged centrally and withdrawing fibers are arranged peripherally. Thus, a countercurrent flow through the cell culture can be achieved.

Preferably, floating ring seals are avoided by using the above-mentioned "tube feeding principle" from a stationary part into a rotating part.

The reactor unit can be a sterile disposable article, which is separated from a non-sterile rotary unit. The sterile disposable article preferably can be sterilized with steam.

Oxygenation preferably is effected externally and is variably adjustable to the oxygen consumption. Thus, the supply of oxygen preferably is effected via the blood plasma or via a nutrient medium. However, an internal oxygenation as shown in FIG. 9 is also conceivable and comprised by the invention. In this embodiment, the reactor unit 12 comprises a housing 20 which forms the first chamber. In the first chamber, hollow fibers 30 are disposed, which are traversed by a liquid medium. In addition, gas transfer fibers 130 are provided, by means of which an oxygenation of the medium contained in the first chamber of the housing 20 is effected. In principle, it is conceivable to also use the hollow gas transfer fibers for removing gaseous substances or also for supplying and/or withdrawing other gases than oxygen.

Thus, the present invention not only comprises an external gas transfer or an external gas supply, but also a gas supply or a gas transfer inside the reactor unit.

Nourishing cells preferably is effected via the blood plasma or nutrient medium.

In a further aspect of the invention, there exists a simple possibility for filling, adding and sampling. In this way, a permanent control of the functionality can be achieved. In addition, there is a possibility for correction or adjustment.

Figure 10:
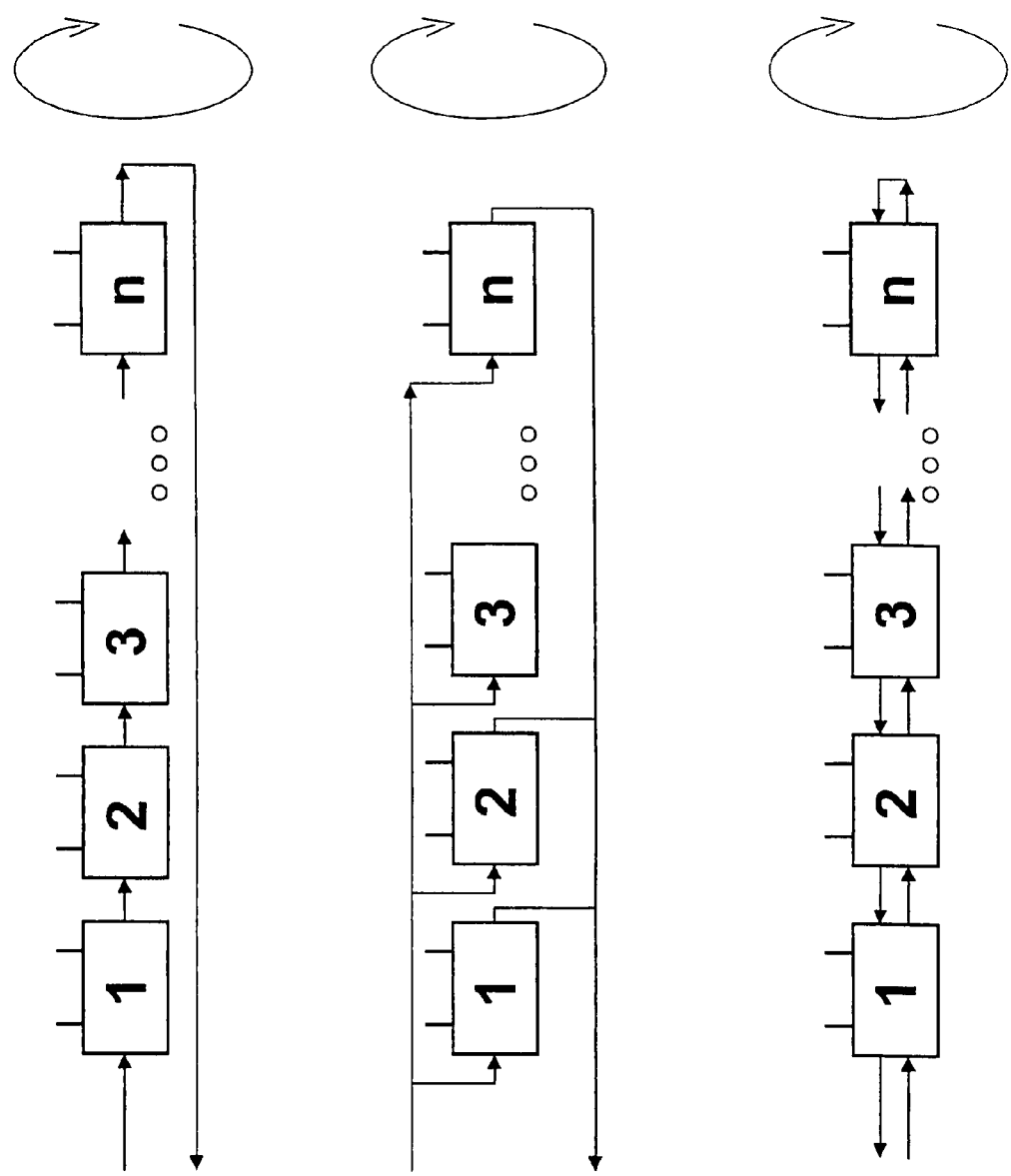

At the top of FIG. 10, a series arrangement of a plurality of reactor units 1-n in the same reactor is shown. As indicated by the arrow, the reactor units are rotatably mounted. The advantages resulting therefrom are as follows:

- cultivating various types of cell in the same reactor in various reactor units;
- uniform supply of various types of cell by the same circuit;
- possibility for specifically delivering intermediate metabolic products from cell type 1 in the reactor unit 1 to cell type 2 in the reactor unit 2. For instance, human liver cells are contained in reactor unit 1 and human kidney cells are contained in reactor unit 2; if a drug is added to the circuit of reactor unit 1, the metabolite formed by the liver cells in reactor unit 1 is supplied directly to the kidney cells contained in reactor unit 2, whereby the further metabolization can be characterized.
- possibility for adding substances or withdrawing intermediate metabolic products at any time on any metabolic stage;
- possibility for withdrawing samples with cell material from the cell chambers at any time, in order to characterize the cell condition;

possibility for determining the influence of chemical, pharmaceutical and cosmetic substances on different types of cell—also in a long-term experiment.

The arrangement in the middle of FIG. 10 shows a parallel arrangement of rotatably mounted reactor units, which thus are not traversed sequentially, but parallel to each other. The advantages resulting therefrom are as follows:

cultivating various types of cell in the same reactor in various reactor units, identical supply of each individual reactor unit with exactly the same nutrient solution in terms of chemical composition, oxygen content, etc., suitability for characterizing for instance batch-to-batch differences of the same cells; example: three reactor units are connected in parallel in the same reactor. Reactor unit 1 contains human liver cells of donor 1, reactor unit 2 contains human liver cells of donor 2, and reactor unit 3 contains human liver cells of donor 3. Due to the parallel arrangement, and with an identical supply, the development of the respective cell cultures can now be characterized. By corresponding sampling from the cell compartment, the development behavior of each batch can be characterized qualitatively and quantitatively. If a drug is added, for instance, to the nutrient medium before entering the reactor units and if the nutrient solutions withdrawn from the reactor units no longer are recirculated, but the metabolites produced from the drug from the respective batch of liver cells are detected in the same, the individual differences in terms of metabolic activity of the same cells with a different cell source (batch) can be determined qualitatively and quantitatively by means of this system.

At the bottom of FIG. 10 a return flow and a transverse flow, respectively, is shown between the likewise rotatably mounted reactor units 1-n. As can be taken from this representation, the reactor units include two inlets and two outlets and are connected with each other such that the outlet of a first reactor unit forms the inlet of a second reactor unit, and the outlet of this second reactor unit forms the inlet of the first reactor unit. This system is also continued between the further reactor units.

The advantages of the arrangement as shown at the bottom of FIG. 10 are as follows:

cultivating various types of cell in the same reactor in various reactor units, by arranging the reactor units with different cell batches (different in terms of type of cell and/or cell source/cell batch) metabolic processes can be simulated in vivo under in-vitro conditions, in contrast to the arrangement as shown at the top of FIG. 10, the nutrient solution withdrawn from the last reactor unit is not recirculated to the reactor unit 1, but to the upstream reactor unit; example: reactor unit 1 contains skin cells, reactor unit 2 contains liver cells, and reactor unit 3 contains virus cells. Upon application of a certain chemical onto the skin cells, a metabolite is formed by the liver cells in reactor unit 2, which can be metabolized by the kidney substances, but cannot be secreted. By recirculation to the liver-cell reactor unit, the direct influence on the activity of the liver cells can be determined.

In principle, a combination of the arrangements, i.e. of series connection and parallel connection, is also conceivable. The advantages of such combination are as follows:

By combining cell chambers and different intermediate steps, highly innovative applications can be realized.

For instance, upon application of a drug into the nutrient medium, the same can be passed over a liver cell culture in a first reactor unit, where a plurality of metabolites are generated. The generation of metabolites is directly followed by a separation of metabolites, e.g. in the form of a chromatographic method. Subsequently, the different metabolites are forwarded to different cells, e.g. in the form of the parallel arrangement, in order to characterize the effect of the different metabolites on different cells.

This means that in dependence on the concrete test set-up, every possible combination between the three arrangements illustrated in FIG. 10 is conceivable and possible.

As can be taken from FIG. 10, the illustrated reactor units are arranged in one reactor. In principle, it is likewise conceivable to use a plurality of reactors, i.e. to not dispose all reactor units in one reactor.

By means of the system illustrated in FIG. 2, an integrated thermostatting of the reactor unit can be effected.

In connection with a therapy or culture, cells of the following origin can be used, for instance:

Primary cells, cells differentiated from stem cells, immortalized cells—each freshly isolated/cultivated and cryopreserved.

In a further aspect of the invention, cell quantities from microquantities up to more than 1 kg can be cultivated.

With a corresponding design, the invention provides the following advantages:

use of polysulfone hollow fibers with a large exchange surface and variably adjustable porosity—better mass transfer when using inert materials clearly more efficient bidirectional mass transfer by convection, in particular for medium-molecular and higher-molecular synthesis products with a low diffusion rate due to the use of hydrophilic and/or hydrophobic membranes, mass transfer better controllable/adjustable due to the separation of the supplying fibers from the withdrawing fibers and a freely variable arrangement of the fibers, improved supply of the cells and hence better cell performance due to counterflow and rotation, additionally improved mixing and mass transport avoidance of floating ring seals by using the "tube feeding principle" from a stationary part into a rotating part—no twisting of tubes (trouble-free operation in clinical use) and no abrasion in the reactor unit due to the possibility for using human body fluids, avoidance of the use of commercial nutrient solutions (for instance RPMI) and hence the contact of non-physiological substances in use separation of sterile disposable article and non-sterile rotary unit—simple handling with high safety for the user disposable article to be sterilized with steam—no toxic decomposition products (ETO) and highest possible safety for the user in terms of microbiological contamination oxygenation and nourishment of the liver cells/pancreas cells inside or outside the rotating unit via the blood plasma/culture medium. In the case of an external oxygenation (only one circuit in the rotating part), no additional membrane in the cell module—thus higher safety for the user easy possibility for filling, adding and sampling; due to the filling method, minimized contamination and hence increased safety for the user due to the possibility for sampling, permanent monitoring of the cells possible—higher safety in terms of functionality and harmlessness (sterility, pH, formation of toxic metabolic products, etc.)

due to the use cryopreserved cells of human origin, independent of the availability of transplants system ready for operation quickly (assembly, availability, cell material) and safely (sterility, user-friendliness).

The invention being thus described, it will be apparent that the same may be varied in many ways. Such variation are not to be regarded as a departure from the spirit and scope of the invention, and all such modifications as would be recognized by one skilled in the art are intended to be included within the scope of the following claims.

What is claimed is:

1. A reactor comprising:
a rotatably mounted reactor unit having a first chamber and a second chamber, with the first chamber being formed by an interior of a housing and the second chamber being formed by an interior of a plurality of hollow fibers arranged in the housing, and with an axis of rotation of the reactor unit being parallel to an axial direction of the hollow fibers,
the reactor unit including
(i) at least two opposed casting compounds in which opposite terminal regions of the hollow fibers are embedded and between which another portion of the hollow fibers extends, with a length of the portion of the hollow fibers extending between the casting compounds being at least 1% greater than a distance between surfaces of the opposed casting compounds so as to provide a bulged or spindle-shaped bundle of the hollow fibers between the casting compounds, and
(ii) an element that constricts the bulged or spindle-shaped bundle of hollow fibers such that a density of the hollow fibers based on a cross-sectional area of the first chamber is increased in a vicinity of the constriction relative to the density of the hollow fibers without using the element, the element that constricts being located along the bulged or spindle-shaped bundle of hollow fibers between the opposed casting compounds.

2. The reactor according to claim 1, wherein the density of the hollow fibers in at least one region of the first chamber, based on the cross-sectional area of the first chamber is from 0.2 to 10 fibers/mm$^2$.

3. The reactor according to claim 1, wherein the density of the hollow fibers based on the cross-sectional area of the first chamber varies in a longitudinal direction of the hollow fibers.

4. The reactor according to claim 1, wherein the reactor unit includes a third chamber, which is formed by an interior of one or more hollow gas transfer fibers arranged in the first chamber.

5. The reactor according to claim 4, wherein the hollow gas transfer fibers have at least one of a larger outside diameter and an inside diameter than the hollow fibers forming the second chamber.

6. The reactor according to claim 4, wherein the hollow gas transfer fibers are configured for a transfer of oxygen via a membrane.

7. The reactor according to claim 1, wherein the hollow fibers are arranged in the housing such that the density of the hollow fibers in at least one region of the first chamber does not exceed 10 fibers/mm$^2$ based on the cross-sectional area of the first chamber.

8. The reactor according to claim 1, wherein the hollow fibers include an inlet and an outlet.

9. The reactor according to claim 1, wherein the housing has a rotationally symmetric configuration.

10. The reactor according to claim 1, wherein the housing has at least one port for filling, evacuating, or sampling from the first chamber.

11. The reactor according to claim 1, wherein an inside diameter of the hollow fibers is not more than 300 μm.

12. The reactor according to claim 1, wherein a hydraulic permeability of a membrane of the hollow fibers is at least 200 ml/mmHg×h×m$^2$.

13. The reactor according to claim 1, wherein a cut-off of a membrane forming the hollow fibers is between $10^4$ and $10^7$ Da.

14. The reactor according to claim 1, wherein the reactor unit has a material of construction that can be sterilized with steam.

15. The reactor according to claim 1, wherein the reactor unit is configured as a disposable unit.

16. The reactor according to claim 1, wherein at least one of the housing having a material of construction of PP, the casting compound having a material of construction of polyurethane, and the hollow fibers having a material of construction of a polysulfone.

17. The reactor according to claim 1, wherein the reactor includes a plurality of said reactor units.

18. The reactor according to claim 17, wherein the plurality of reactor units are arranged in series or in parallel.

19. The reactor according to claim 18, wherein the plurality of reactor units are arranged in series, such that a mass transfer between two adjacent reactors is only possible in one, or simultaneously in two directions.

20. The reactor according to claim 17, wherein the reactor units are configured without a floating ring seal.

21. A method for effecting a mass transfer via one or more of the hollow fibers with the reactor according to claim 1, wherein a pressure in the second chamber associated with the interior of the hollow fibers and in the first chamber associated with the housing is adjusted such that the mass transfer through the hollow fibers is at least partly effected by convection.

22. The method according to claim 21, wherein pressure ratios between the first and the second chamber are chosen such that convective mass transport in one portion of the hollow fibers is effected from a medium contained in the hollow fibers into medium contained in the housing, and in another portion of the hollow fibers is effected from the medium received in the housing into the medium contained in the hollow fibers.

23. A system with a reactor according to claim 1, further comprising
a reservoir connected with the reactor unit such that from the reservoir a medium is introduced into the second chamber of the reactor unit formed by the hollow fibers or is withdrawn from the second chamber,
a delivery pump for delivering the medium, and
an oxygenator for enriching the medium delivered with oxygen.

24. The system according to claim 23, wherein the oxygenator is provided upstream of the reactor in a flow direction of the medium.

25. The system according to claim 23, further comprising a heater for heating the medium provided upstream of the reactor in a flow direction.

26. The system according to claim 23, wherein the delivery pump is a peristaltic pump.

27. The reactor according to claim 2, wherein the density of the hollow fibers in the at least one region of the first chamber, based on the cross-sectional area of the first chamber, is from 0.5 to 6 fibers/mm$^2$.

28. The reactor according to claim 2, wherein the density of the hollow fibers in the at least one region of the first chamber, based on the cross-sectional area of the first chamber, is from 1 to 4 fibers/mm$^2$.

29. The reactor according to claim 1, wherein the length of the portion of the hollow fibers located between the casting compounds is at least 3%.

30. The reactor according to claim 6, wherein the hollow gas transfer fibers have a material of construction that is PTFE or that includes PTFE.

31. The reactor according to claim 9, wherein the housing is cylindrical.

32. The reactor according to claim 11, wherein the inside diameter of the hollow fibers is not more than 200 µm.

33. The reactor according to claim 11, wherein the inside diameter of the hollow fibers is not more than 100 µm.

34. The reactor according to claim 12, wherein the hydraulic permeability of the membrane of the hollow fibers is at least 500 ml/mmHg×h×m$^2$.

35. The reactor according to claim 13, wherein the cut-off of the membrane forming the hollow fibers is between $10^5$ and $10^6$ Da.

36. The reactor according to claim 13, wherein the cut-off of the membrane forming the hollow fibers is between 700,000 and 900,000 Da.

37. The reactor according to claim 16, wherein the hollow fibers have a material of construction of a polyaryl ether sulfone.

38. The reactor according to claim 16, wherein the hollow fibers have a material of construction of a polysulfone hydrophilized with PVP.

39. The reactor according to claim 1, wherein the element that constricts the bulged or spindle-shaped bundle of the hollow fibers is an O-ring.

40. A reactor unit for a reactor, the reactor unit comprising:
a first chamber and a second chamber, with the first chamber being formed by an interior of a housing and the second chamber being formed by an interior of a plurality of hollow fibers arranged in the housing;
at least two opposed casting compounds in which opposite terminal regions of the hollow fibers are embedded and between which another portion of the hollow fibers extends, with a length of the portion of the hollow fibers extending between the casting compounds being at least 1% greater than a distance between surfaces of the opposed casting compounds so as to provide a bulged or spindle-shaped bundle of the hollow fibers between the casting compounds; and
an element that constricts the bulged or spindle-shaped bundle of hollow fibers such that a density of the hollow fibers based on a cross-sectional area of the first chamber is increased in a vicinity of the constriction relative to the density of the hollow fibers without using the element, the element that constricts being located along the bulged or spindle-shaped bundle of hollow fibers between the opposed casting compounds.

41. The reactor unit according to claim 40, wherein the reactor unit is rotatably mounted in the reactor.

42. The reactor according to claim 1, wherein the density of the hollow fibers in at least one region of the first chamber, based on the cross-sectional area of the first chamber is from 3.9 to 12 fibers/mm$^2$.

43. The reactor unit according to claim 40, wherein the density of the hollow fibers in at least one region of the first chamber, based on the cross-sectional area of the first chamber is from 3.9 to 12 fibers/mm$^2$.

* * * * *

UNITED STATES PATENT AND TRADEMARK OFFICE
CERTIFICATE OF CORRECTION

PATENT NO.       : 8,557,571 B2                                     Page 1 of 1
APPLICATION NO. : 11/794234
DATED            : October 15, 2013
INVENTOR(S)      : Kugelmann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1402 days.

Signed and Sealed this
Fifteenth Day of September, 2015

Michelle K. Lee
*Director of the United States Patent and Trademark Office*